(12) United States Patent
Curstedt et al.

(10) Patent No.: US 7,842,664 B2
(45) Date of Patent: **\*Nov. 30, 2010**

(54) SYNTHETIC LIPID MIXTURES FOR THE PREPARATION OF A RECONSTITUTED SURFACTANT

(75) Inventors: Tore Curstedt, Parma (IT); Jan Johansson, Parma (IT); Bengt Robertson, Parma (IT)

(73) Assignee: Chiesi Farmaceutici S.p.A, Parma (IT)

( \* ) Notice: Subject to any disclaimer, the term of this patent is extended or adjusted under 35 U.S.C. 154(b) by 0 days.

This patent is subject to a terminal disclaimer.

(21) Appl. No.: 12/043,177

(22) Filed: Mar. 6, 2008

(65) Prior Publication Data

US 2008/0242589 A1 Oct. 2, 2008

Related U.S. Application Data

(63) Continuation of application No. 10/512,869, filed as application No. PCT/EP03/04937 on May 12, 2003, now Pat. No. 7,511,011.

(30) Foreign Application Priority Data

May 17, 2002 (IT) .......................... MI2002A1058

(51) Int. Cl.
*A61K 38/02* (2006.01)
(52) U.S. Cl. .......................................... 514/2; 530/300
(58) Field of Classification Search ........................ None
See application file for complete search history.

(56) References Cited

U.S. PATENT DOCUMENTS 5,653,996 A \* 8/1997 Hsu ............................ 424/450

5,952,303 A 9/1999 Bornstein et al.
7,053,044 B1 \* 5/2006 Curstedt et al. ................. 514/2
7,511,011 B2 \* 3/2009 Curstedt et al. ................. 514/2
2009/0075892 A1 3/2009 Johansson et al.
2009/0088379 A1 4/2009 Johansson et al.

FOREIGN PATENT DOCUMENTS

WO 00/47623 8/2000
WO WO 00/47623 \* 8/2000
WO 01/76619 10/2001

OTHER PUBLICATIONS

Palmblad, J. of Biochem., 1999, vol. 338, pp. 381-386.\*
Yu, Shou-Hwa et al., "Effect of plumonary surfactant protein B (SP-B) and calcium on phospholipid adsorption and squeez-out of phosphatidylglycerol from binary phospholipid monolayers containing dipalmitoylphosphatidylcholine" Biochimica Et Biophysica Acta. Netherlands, vol. 1126, No. 1, pp. 26-34, Jun. 5, 1992.
U.S. Appl. No. 12/422,581, filed Apr. 13, 2009, Johansson, et al.

\* cited by examiner

*Primary Examiner*—Christopher R. Tate
*Assistant Examiner*—Roy Teller
(74) *Attorney, Agent, or Firm*—Oblon, Spivak, McClelland, Maier & Neustadt, L.L.P.

(57) ABSTRACT

The invention relates to reconstituted surfactants consisting of artificial phospholipids and peptides able to lower the air-liquid surface tension, more particularly to reconstituted surfactants comprising special phospholipid mixtures and artificial peptides which are analogues of the natural surfactant SP-C protein for the treatment of respiratory distress syndrome (RDS) and other diseases relating to pulmonary surfactant dysfunctions.

20 Claims, No Drawings

SEQUENCE LISTING

```
<160> NUMBER OF SEQ ID NOS: 6

<210> SEQ ID NO 1
<211> LENGTH: 101
<212> TYPE: PRT
<213> ORGANISM: Artificial Sequence
<220> FEATURE:
<223> OTHER INFORMATION: synthetic peptide
<220> FEATURE:
<221> NAME/KEY: misc_feature
<222> LOCATION: (1)..(1)
<223> OTHER INFORMATION: The amino acid can be present or absent
<220> FEATURE:
<221> NAME/KEY: misc_feature
<222> LOCATION: (2)..(2)
<223> OTHER INFORMATION: The amino acid can be present or absent
<220> FEATURE:
<221> NAME/KEY: misc_feature
<222> LOCATION: (4)..(4)
<223> OTHER INFORMATION: Xaa is S optionally substituted with acyl
      groups containing 12-22 carbon atoms linked to the side chain via
      an ester or thio-ester bond
<220> FEATURE:
<221> NAME/KEY: misc_feature
<222> LOCATION: (5)..(5)
<223> OTHER INFORMATION: Xaa is S optionally substituted with acyl
      groups containing 12-22 carbon atoms linked to the side chain via
      an ester or thio-ester bond
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa is I, L, or nL
<220> FEATURE:
<221> NAME/KEY: misc_feature
<222> LOCATION: (14)..(31)
<223> OTHER INFORMATION: Xaa may be present or absent and if present is
      I, L or nL
<220> FEATURE:
<221> NAME/KEY: misc_feature
<222> LOCATION: (32)..(51)
<223> OTHER INFORMATION: Xaa may be present or absent and if present is
      I, L or nL
<220> FEATURE:
<221> NAME/KEY: misc_feature
<222> LOCATION: (52)..(52)
<223> OTHER INFORMATION: Xaa can be any naturally occurring amino acid
<220> FEATURE:
<221> NAME/KEY: misc_feature
<222> LOCATION: (53)..(73)
<223> OTHER INFORMATION: Xaa may be present or absent and if present is
      I, L, or nL
<220> FEATURE:
<221> NAME/KEY: misc_feature
<222> LOCATION: (74)..(74)
<223> OTHER INFORMATION: Xaa may be present or absent and if present is
      K, W, F, Y or ornithine
<220> FEATURE:
<221> NAME/KEY: misc_feature
<222> LOCATION: (75)..(94)
<223> OTHER INFORMATION: Xaa may be present or absent and if present is
      K, W, F, Y or ornithine
```

```
<220> FEATURE:
<221> NAME/KEY: misc_feature
<222> LOCATION: (99)..(99)
<223> OTHER INFORMATION: Xaa is M, I, L or nL

<400> SEQUENCE: 1

Phe Gly Ile Pro Xaa Xaa Pro Val His Leu Lys Arg Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
                20                  25                  30

Xaa Xaa Xaa Xaa Xaa Xaa Xaa Xaa Xaa Xaa Xaa Xaa Xaa Xaa Xaa Xaa
            35                  40                  45

Xaa Xaa Xaa Xaa Xaa Xaa Xaa Xaa Xaa Xaa Xaa Xaa Xaa Xaa Xaa Xaa
        50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Gly Ala
                85                  90                  95

Leu Leu Xaa Gly Leu
            100

<210> SEQ ID NO 2
<211> LENGTH: 33
<212> TYPE: PRT
<213> ORGANISM: Artificial Sequence
<220> FEATURE:
<223> OTHER INFORMATION: synthetic peptide
<220> FEATURE:
<221> NAME/KEY: misc_feature
<222> LOCATION: (31)..(31)
<223> OTHER INFORMATION: Xaa can be any naturally occurring amino acid
<220> FEATURE:
<221> NAME/KEY: misc_feature
<222> LOCATION: (32)..(32)
<223> OTHER INFORMATION: Xaa is M, I, L, or nL

<400> SEQUENCE: 2

Ile Pro Ser Ser Pro Val His Leu Lys Arg Leu Lys Leu Leu Leu Leu
1               5                   10                  15

Leu Leu Leu Leu Ile Leu Leu Leu Ile Leu Gly Ala Leu Leu Xaa Gly
                20                  25                  30

Leu

<210> SEQ ID NO 3
<211> LENGTH: 33
<212> TYPE: PRT
<213> ORGANISM: Artificial Sequence
<220> FEATURE:
<223> OTHER INFORMATION: synthetic peptide

<400> SEQUENCE: 3

Ile Pro Ser Ser Pro Val His Leu Lys Arg Leu Lys Leu Leu Leu Leu
1               5                   10                  15

Leu Leu Leu Leu Ile Leu Leu Leu Ile Leu Gly Ala Leu Leu Met Gly
                20                  25                  30

Leu

<210> SEQ ID NO 4
<211> LENGTH: 33
<212> TYPE: PRT
<213> ORGANISM: Artificial Sequence
<220> FEATURE:
<223> OTHER INFORMATION: synthetic peptide
```

-continued

```
<400> SEQUENCE: 4

Ile Pro Ser Ser Pro Val His Leu Lys Arg Leu Lys Leu Leu Leu Leu
1               5                   10                  15

Leu Leu Leu Leu Ile Leu Leu Leu Ile Leu Gly Ala Leu Leu Ile Gly
                20                  25                  30

Leu

<210> SEQ ID NO 5
<211> LENGTH: 33
<212> TYPE: PRT
<213> ORGANISM: Artificial Sequence
<220> FEATURE:
<223> OTHER INFORMATION: synthetic peptide

<400> SEQUENCE: 5

Ile Pro Ser Ser Pro Val His Leu Lys Arg Leu Lys Leu Leu Leu Leu
1               5                   10                  15

Leu Leu Leu Leu Ile Leu Leu Leu Ile Leu Gly Ala Leu Leu Leu Gly
                20                  25                  30

Leu

<210> SEQ ID NO 6
<211> LENGTH: 33
<212> TYPE: PRT
<213> ORGANISM: Artificial Sequence
<220> FEATURE:
<223> OTHER INFORMATION: synthetic peptide
<220> FEATURE:
<221> NAME/KEY: misc_feature
<222> LOCATION: (31)..(31)
<223> OTHER INFORMATION: Xaa is nL

<400> SEQUENCE: 6

Ile Pro Ser Ser Pro Val His Leu Lys Arg Leu Lys Leu Leu Leu Leu
1               5                   10                  15

Leu Leu Leu Leu Ile Leu Leu Leu Ile Leu Gly Ala Leu Leu Xaa Gly
                20                  25                  30

Leu
```

SYNTHETIC LIPID MIXTURES FOR THE PREPARATION OF A RECONSTITUTED SURFACTANT

CROSS-REFERENCE TO RELATED APPLICATIONS

The present application is a continuation of U.S. patent application Ser. No. 10/512,869, filed on Apr. 19, 2005, now U.S. Pat. No. 7,511,011, which is a 35 U.S.C. §371 National Stage patent application of International patent application PCT/EP03/04937, filed on May 12, 2003, which claims priority to Italian patent application MI02A001058, filed on May 17, 2002.

The present invention relates to reconstituted surfactants consisting of phospholipids and artificial peptides able to lower surface tension at the air-liquid interface. In particular, the invention relates to reconstituted surfactants comprising particular phospholipid mixtures and artificial peptide analogues of the natural surfactant SP-C protein for the treatment of respiratory distress syndrome (RDS) and other diseases related to pulmonary surfactant dysfunctions.

BACKGROUND OF THE INVENTION

Pulmonary surfactant lowers the surface tension arising at the air-liquid interface of the internal alveolar wall, thus preventing the lungs from collapsing at the end of expiration. Surfactant deficiency is a dysfunction which commonly affects preterm infants and causes RDS, a disease which can be effectively treated with natural surfactants extracted from animal lungs. The main constituents of these surfactant preparations are phospholipids, such as 1,2-dipalmitoyl-sn-glycero-3-phosphocholine commonly known as di-palmitoyl-phosphatidyl-choline (DPPC), phosphatidylglycerol (PG) and surfactant hydrophobic proteins B and C (SP-B and SP-C). The hydrophilic surfactant proteins SP-A and SP-D, which are C-type ($Ca^{2+}$-dependent) collagenous lectins and thought to act primarily in the host-defence system, are normally not included in the surfactant preparations due to the organic solvent extraction procedures employed. Modified natural surfactant preparations obtained from animal tissues are used in current therapeutical practice. These preparations usually consist of the aforementioned components with the exception of hydrophilic proteins, which are removed upon extraction with organic solvents.

Owing to the drawbacks of the surfactant preparations from animal tissues, such as the complexity of the manufacturing and sterilization processes and possible induction of immune reactions, attempts to prepare artificial surfactants have been made.

In the strict sense of the word, artificial surfactants are mixtures of phospholipids only or mixtures of phospholipids and other synthetic lipids. Reconstituted surfactants are artificial surfactants added with hydrophobic proteins—either isolated from animal tissues or obtained through recombinant techniques—or synthetic peptidic derivatives of such proteins.

The properties and the activity of reconstituted surfactants greatly depend not only on the protein/peptide components, but also on the composition of the phospholipid mixture.

DESCRIPTION OF THE INVENTION

It has now been found that dipalmitoyl phosphatidylcholine (DPPC) in admixture with specific palmitoyl oleyl phospholipids is an ideal vehicle for the artificial peptides commonly used in reconstituted surfactants as analogues of natural surfactant proteins SP-C and/or SP-B. In particular, reconstituted surfactants comprising the SP-C analogues disclosed in WO 00/47623 in combination with DPPC and a palmitoyl oleyl phospholipid—preferably selected from palmitoyl oleyl phosphatidylglycerol (POPG) or a mixture of POPG with palmitoyl oleyl phosphatidylcholine (POPC)—in weight ratios ranging from 80:20 to 60:40 have been found to lower the surface tension and the viscosity of the preparations obtained therefrom. Contrary to what is reported in the literature, it has also surprisingly been found that the addition of palmitic acid (PA) is useless and, what's more, in some cases can lower the in vivo surfactant's activity.

Accordingly, the present invention relates to reconstituted surfactants comprising mixtures essentially consisting of dipalmitoyl phosphatidylcholine (DPPC) and palmitoyl oleyl phosphatidylglycerol (POPG) or a mixture thereof with palmitoyl oleyl phosphatidylcholine (POPC) in weight ratios ranging from 80:20 to 60:40 and artificial peptide analogues of natural surfactant proteins SP-C and/or SP-B. The surfactant of the invention is devoid of palmitic acid.

The weight ratio between DPPC and POPG ranges preferably from 75:25 to 65:35, and is more preferably 68:31. In the case of DPPC:POPG:POPC mixtures, the phospholipids are preferably used in weight ratios of 60:20:20 or 68:15:16.

Any artificial peptide analogue of natural surfactant proteins SP-C and/or SP-B can be advantageously used, such as those disclosed in WO 89/06657, WO 92/22315 and WO 95/32992. Preferred is the use of SP-C analogues having the following general formula (I), the amino acids being represented with the one-letter code, (SEQ ID NO: 1)
$F_eG_fIPZZPVHLKR(X_aB)(X_bB)_n(X_cB)_m X_dGALL\Omega GL$ (I)

wherein:
X is an amino acid selected from the group consisting of I, L, nL (norleucine);
B is an amino acid selected from the group consisting of K, W, F, Y, ornithine;
Z is S optionally substituted with acyl groups containing 12-22 carbon atoms linked to the side chain via an ester or thio-ester bond, respectively;
$\Omega Q$ is an amino acid selected from the group consisting of M, I, L, nL;
a is an integer from 1 to 19;
b is an integer from 1 to 19;
c is an integer from 1 to 21;
d is an integer from 0 to 20;
e is 0 or 1;
f is 0 or 1;
n is 0 or 1;
m is 0 or 1;

with the following provisos:
n+m>0;
f≧e,
$(X_aB)_n(X_bB)_n(X_cB)_m X_d$ is a sequence having a maximum of 22 amino acids, preferably from 10 to 22.

Even more preferred is the use of peptides of formula (II)

(SEQ ID NO: 2)
IPSSPVHLKRLKLLLLLLLLILLLILGALLΩGL (II)

wherein:

Ω is an amino acid selected from the group consisting of M, I, L, nL and wherein serine can optionally be acylated, for example with palmitoyl.

The hereinafter reported peptide (SP-C33), in the non-acylated form, is the most preferred of the invention, (SEQ ID NO: 3)
IPSSPVHLKRLKLLLLLLLLILLLILGALLMGL  (SP-C33)

Peptides of formula (I) may be prepared by means of conventional peptide synthesis or recombinant techniques as disclosed in WO 00/47623.

Acylated peptides are preferably synthesized by reacting the peptides with an acyl chloride in pure trifluoroacetic acid for 10 hours at room temperature, followed by quenching with 80% aqueous ethanol.

The activity of the reconstituted surfactants of the invention in reducing surface tension has been evaluated both in vitro and in vivo. In particular, the in vivo results clearly show that the reconstituted surfactants of the present invention are able to increase tidal volume—which is in turn an index of the pulmonary expansion capacity—in a significantly higher extent than the surfactants obtained with the mixtures of DPPC, PG and PA commonly used in the prior art.

The reconstituted surfactants of the invention may comprise SP-B or polymixins, in particular polimixin B, as SP-B analogues.

The surfactant can be prepared by mixing solutions or suspensions of peptides and phospholipids and by subsequently drying the mixture. If necessary, the dried mixture can be re-suspended, dispersed or administrated as such to subjects which require a treatment for surfactant deficiency.

In the case of aerosol administration, it will be necessary to combine small surfactant particles with a suitable inert propellant. Other administration forms, such as vapourisation or nebulization of stable surfactant solutions/suspensions, are also within the scope of the present invention.

The following examples illustrate the invention in greater detail.

EXAMPLES

Experimental Section

Materials 1,2-Dipalmitoyl-sn-glycero-3-phosphocholine (DPPC), 1-palmitoyl-2-oleoyl-sn-glycero-3-phosphocholine (POPC), 1-palmitoyl-2-oleoyl-sn-glycero-3-phosphoglycerol (POPG), egg phosphatidylglycerol (PG), palmitic acid (PA), and polymyxin B (PxB) sulfate were utilized to prepare the following lipid mixtures and weight ratios: DPPC/PG/PA, 68:22:9; DPPC/POPG/PA, 68:22:9; DPPC/POPC/POPG, 60:20:20; DPPC/POPG/POPC/PA, 57:19:19:5; DPPC/POPC/POPG, 68:16:15 and DPPC/POPG, 68:31.

SP-C33 was synthesized and purified as described in WO 00/47623.

Preparation of Synthetic Surfactants

SP-C33 and lipids in peptide/lipid weight ratios of 0.02:1 were mixed in chloroform/methanol 98:2 (v/v), the solvents were evaporated and the resulting peptide/lipid films were subsequently hydrated in 150 mM NaCl by repeated sonication, at a lipid concentration of 80 or 35 mg/ml. The surfactant samples used for analyses in the pulsating bubble surfactometer were diluted in saline to working concentrations (10 mg/ml surfactant). In some experiments PxB was added up to a final concentration of 2% (w/w) of the lipid concentration. The surfactant which contained SP-C33 in DPPC/PG/PA (68:22:9) provided very viscous suspensions at 80 mg/ml and was difficult to administer to the experimental animals.

Two well known modified natural surfactants, Curosurf (Chiesi Farmaceutici) and Survanta (Abbott) were administered according to the manufacturer's instructions. Curosurf was suspended at 80 mg/ml and 2.5 ml/kg body weight was administered; Survanta was suspended at 25 mg/ml and 4 ml/kg body weight was administered.

Pulsating Bubble Experiments

The dynamic surface properties of SP-C33 surfactants with and without 2% (w/w) PxB were evaluated by a pulsating bubble surfactometer. For these experiments, the surfactant was suspended in saline at a concentration of 10 mg/ml and analysed at 37° C. The sensitivity towards inhibition was tested by adding 40 mg/ml albumin to the surfactant suspension. A bubble communicating with ambient-air was created in a plastic test chamber containing approximately 20 μl of the sample fluid. The bubble radius was oscillated at a rate of 40 cycles/min. from a maximum of 0.55 to a minimum of 0.40 mm, corresponding to a 50% cyclic surface compression. Surface tension values at minimum and maximum bubble size ($\gamma_{min}$, $\gamma_{max}$) were recorded over 5 min. pulsations.

In Vivo Experiments

The surfactant mixtures were assayed in premature newborn rabbits, obtained by hysterectomy at the gestational age of 27 days (term: 31 days). The animals were tracheotomized at birth, kept in plethysmography boxes at 37° C. and ventilated in parallel with 100% oxygen at a frequency of 40 breaths/min. and a 50% inspiration time. Treated animals received 2.5 ml/kg or 4 ml/kg of the above surfactant preparation through a tracheal cannula. Littermates which did not receive any surfactant preparation were used as controls. After instilling the surfactant, peak pressure was first raised to 35 cmH$_2$O per 1 min., to facilitate the distribution of the surfactant in the lungs, then lowered to 25 cmH$_2$O. The animals were then ventilated with a peak pressure of 25 cmH$_2$O for 15 min., thereafter the pressure was lowered first to 20 cmH$_2$O for 5 min., then to 15 cmH$_2$O for 5 min. and raised again to 25 cmH$_2$O for 5 min. Tidal volumes were measured at 5 min. intervals with a pneumotachograph connected to each plethysmograph box.

At the end of the established ventilation period, the animals were sacrificed by intracerebral lidocain injection. Their abdomen was opened and the diaphragm position was inspected for pneumotorax evidences.

Example 1

SP-C33 In Vitro Superficial Activity in Different Lipid Mixtures

The dynamic surface properties of 2% (w/w) SP-C33 in DPPC/PG/PA (68:22:9), DPPC/POPC/POPG (60:20:20), DPPC/POPC/POPG (68:16:15) and DPPC/POPG (68:31) were evaluated with a pulsating bubble surfactometer, which showed $\gamma_{min}$<2 mN/m after 5 min. pulsation for all the mixtures and $\gamma_{max}$<40 mN/m for all the mixtures except for SP-C33 in DPPC/PG/PA (68:22:9), whose $\gamma_{max}$ was 48 mN/m.

Example 2

In Vivo Optimal Effect without PA

To evaluate the relevance of the lipid composition, we compared the in vivo effects of SP-C33 in the mixtures DPPC/PG/PA (68:22:9), DPPC/POPG/PA (68:22:9) and DPPC/POPG (68:31). SP-C33 in DPPC/POPG (68:31) showed a higher effect than the other two mixtures. The data showed a marked increase in tidal volumes after treatment with SP-C33 in DPPC/POPG (68:31). They also showed that, if the DPPC and acid lipid content is constant, the presence of PA reduces the effect of the treatment. A negative effect of PA on the in vivo activity of the SP-C33-based surfactant is further confirmed by the effect ($V_T$=12 a 15 min. e $V_T$=14 a 25 min.) of SP-C33 in DPPC/POPC/POPG/PA (57:19:19:5) which is slightly lower than that of SP-C33 in DPPC/POPC/POPG (60:20:20).

The invention claimed is:

1. A reconstituted surfactant, consisting of:
   a) a phospholipid vehicle;
   b) an artificial peptide analog of natural surfactant protein SP-C; and
   c) an artificial peptide analog of natural surfactant protein SP-B,
   wherein said vehicle is a mixture consisting of: (i) dipalmitoyl phophatidylcholine (DPPC) and (ii) a palmitoyl oleyl phospholipid selected from the group consisting of 1 palmitoyl-2-oleoyl-sn-glycero-3-phosphoglycerol (POPG) and a mixture of 1 palmitoyl-2-oleoyl-sn-glycero-3-phosphoglycerol and 1 palmitoyl-2-oleoyl-sn-3-glycero-3-phosphocholine (POPC), in a weight ratio ranging from 80:20 to 60:40, and
   wherein said artificial peptide analog of natural surfactant protein SP-C has the formula (II):

IPSSPVHLKRLKLLLLLLLLILLLILGALLΩGL (II) (SEQ ID NO: 2)

wherein Ω is a residue selected from the group consisting of M, I, L and nL.

2. A reconstituted surfactant according to claim 1, which comprises DPPC and POPG in a weight ratio of 75:25 to 65:35.

3. A reconstituted surfactant according to claim 2, which comprises DPPC and POPG in a weight ratio of 68:31.

4. A reconstituted surfactant according to claim 1, which comprises DPPC, POPG, and POPC in a weight ratio of 60:20:20 to 68:15:16.

5. A process for preparing a reconstituted surfactant according to claim 1, comprising:
   i) mixing a solution or a suspension of the two artificial peptides and the phospholipid vehicle; and
   ii) drying the mixture.

6. A dispersion, a suspension or a dry powder, comprising a reconstituted surfactant according to claim 1.

7. A method for the treatment of one or more diseases related to a pulmonary surfactant dysfunction, said method comprising administering an effective amount of a reconstituted surfactant according to claim 1 to a patient in need thereof.

8. A method according to claim 7, wherein the disease is respiratory distress syndrome.

9. A reconstituted surfactant according to claim 1, wherein said artificial peptide analog of natural surfactant protein SP-C is

```
                                   (SEQ ID NO: 4)
IPSSPVHLKRLKLLLLLLLLILLLILGALLIGL.
```

10. A reconstituted surfactant according to claim 1, wherein said artificial peptide analog of natural surfactant protein SP-C is

```
                                   (SEQ ID NO: 5)
IPSSPVHLKRLKLLLLLLLLILLLILGALLLGL.
```

11. A reconstituted surfactant according to claim 1, wherein said artificial peptide analog of natural surfactant protein SP-C is

```
                                   (SEQ ID NO: 6)
IPSSPVHLKRLKLLLLLLLLILLLILGALLnLGL.
```

12. A reconstituted surfactant according to claim 9, which comprises DPPC and POPG in a weight ratio of 75:25 to 65:35.

13. A reconstituted surfactant according to claim 9, which comprises DPPC and POPG in a weight ratio of 68:31.

14. A reconstituted surfactant according to claim 9, which comprises DPPC, POPG, and POPC in a weight ratio of 60:20:20 to 68:15:16.

15. A reconstituted surfactant according to claim 10, which comprises DPPC and POPG in a weight ratio of 75:25 to 65:35.

16. A reconstituted surfactant according to claim 10, which comprises DPPC and POPG in a weight ratio of 68:31.

17. A reconstituted surfactant according to claim 10, which comprises DPPC, POPG, and POPC in a weight ratio of 60:20:20 to 68:15:16.

18. A reconstituted surfactant according to claim 11, which comprises DPPC and POPG in a weight ratio of 75:25 to 65:35.

19. A reconstituted surfactant according to claim 11, which comprises DPPC and POPG in a weight ratio of 68:31.

20. A reconstituted surfactant according to claim 11, which comprises DPPC, POPG, and POPC in a weight ratio of 60:20:20 to 68:15:16.

* * * * *